US010224489B2

(12) United States Patent
Chen et al.

(10) Patent No.: US 10,224,489 B2
(45) Date of Patent: Mar. 5, 2019

(54) COMPOUND AND ORGANIC ELECTRONIC DEVICE USING THE SAME

(71) Applicant: Nichem Fine Technology Co., Ltd., Hsinchu County (TW)

(72) Inventors: Chien-Tien Chen, Hsinchu County (TW); Chi-Chung Chen, Hsinchu County (TW)

(73) Assignee: NICHEM FINE TECHNOLOGY CO., LTD., Jhubei (TW)

( * ) Notice: Subject to any disclaimer, the term of this patent is extended or adjusted under 35 U.S.C. 154(b) by 137 days.

(21) Appl. No.: 15/228,583

(22) Filed: Aug. 4, 2016

(65) Prior Publication Data

US 2017/0040545 A1 Feb. 9, 2017

Related U.S. Application Data

(60) Provisional application No. 62/200,929, filed on Aug. 4, 2015.

(51) Int. Cl.

| | | |
|---|---|---|
| *H01L 51/54* | (2006.01) | |
| *C09K 11/06* | (2006.01) | |
| *H01L 51/00* | (2006.01) | |
| *C07D 235/02* | (2006.01) | |
| *C07D 403/14* | (2006.01) | |
| *C07D 401/14* | (2006.01) | |
| *C07C 255/52* | (2006.01) | |
| *C07F 9/53* | (2006.01) | |
| *C07C 211/58* | (2006.01) | |
| *C07D 209/86* | (2006.01) | |
| *C07D 213/06* | (2006.01) | |
| *C07D 235/20* | (2006.01) | |
| *C07D 251/24* | (2006.01) | |
| *C07D 471/04* | (2006.01) | |
| *C07D 487/04* | (2006.01) | |
| *C07F 5/02* | (2006.01) | |
| *C09K 11/02* | (2006.01) | |

(Continued)

(52) U.S. Cl.
CPC ........ *H01L 51/0072* (2013.01); *C07C 211/58* (2013.01); *C07C 255/52* (2013.01); *C07D 209/86* (2013.01); *C07D 213/06* (2013.01); *C07D 221/20* (2013.01); *C07D 235/02* (2013.01); *C07D 235/20* (2013.01); *C07D 251/24* (2013.01); *C07D 401/14* (2013.01); *C07D 403/14* (2013.01); *C07D 471/04* (2013.01); *C07D 471/10* (2013.01); *C07D 487/04* (2013.01); *C07F 5/027* (2013.01); *C07F 9/5329* (2013.01); *C09K 11/025* (2013.01); *C09K 11/06* (2013.01); *H01L 51/006* (2013.01); *H01L 51/008* (2013.01); *H01L 51/0052* (2013.01); *H01L 51/0056* (2013.01); *H01L 51/0058* (2013.01); *H01L 51/0061* (2013.01); *H01L 51/0067* (2013.01); *C07C 2603/32* (2017.05); *C09K 2211/1007* (2013.01); *C09K 2211/1014* (2013.01); *C09K 2211/1029* (2013.01); *C09K 2211/1044* (2013.01); *H01L 51/0096* (2013.01); *H01L 51/424* (2013.01); *H01L 51/44* (2013.01); *H01L 51/5056* (2013.01); *H01L 51/5072* (2013.01); *H01L 51/5096* (2013.01); *Y02E 10/549* (2013.01)

(58) Field of Classification Search
CPC ..... Y02E 10/549; C09K 11/06; C09K 11/025; C09K 2211/00; C09K 2211/10; C09K 2211/1007; C09K 2211/1014; C09K 2211/1029; C09K 2211/1044; C07D 235/02; C07D 235/20; C07D 213/06; C07D 251/24; C07D 401/00; C07D 401/14; C07D 403/00; C07D 403/14; C07D 471/00; C07D 471/04; C07D 471/10; C07D 487/00; C07D 487/04; C07D 487/10; C07D 209/86; C07D 221/20; C07C 2603/32; C07C 255/52; C07C 211/58; H01L 51/0032; H01L 51/005; H01L 51/0052; H01L 51/0056; H01L 51/0058; H01L 51/006; H01L 51/0061; H01L 51/0067; H01L 51/0072; H01L 51/008; H01L 51/0096; H01L 51/424; H01L 51/44; H01L 51/50; H01L 51/5012; H01L 51/5016; H01L 51/5056; H01L 51/5072; H01L 51/5096
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | | |
|---|---|---|---|---|
| 2006/0255332 A1* | 11/2006 | Becker | .................. | C09K 11/06 257/40 |
| 2007/0176174 A1 | 8/2007 | Lee et al. | | |
| 2013/0113367 A1 | 5/2013 | Jung et al. | | |

FOREIGN PATENT DOCUMENTS

| | | | |
|---|---|---|---|
| CN | 103468245 A | * | 12/2013 |
| CN | 104387222 A | | 3/2015 |

(Continued)

OTHER PUBLICATIONS

Machine translation of CN 103468245. (Year: 2013).*

*Primary Examiner* — Andrew K Bohaty
(74) *Attorney, Agent, or Firm* — Muncy, Geissler, Olds & Lowe, P.C.

(57) ABSTRACT

A novel compound is disclosed, which comprises: a 7-membered ring segment, which is formed by a cis-stilbene segment and a bridge atom with four bonds; and a fluorene segment connecting to the bridge atom with a double bond. In addition, an organic electronic device is also disclosed, and an organic layer therein comprises the novel compound of the present invention.

12 Claims, 2 Drawing Sheets

(51) Int. Cl.
   *C07D 221/20* (2006.01)
   *C07D 471/10* (2006.01)
   *H01L 51/50* (2006.01)
   *H01L 51/44* (2006.01)
   *H01L 51/42* (2006.01)

(56) References Cited

FOREIGN PATENT DOCUMENTS

| | | |
   |---|---|---|
   | TW | 576863 B | 2/2004 |
   | TW | I466849 B | 1/2015 |
   | TW | I485145 B | 5/2015 |

\* cited by examiner

COMPOUND AND ORGANIC ELECTRONIC DEVICE USING THE SAME

CROSS REFERENCE TO RELATED APPLICATION

This application claims the benefit of filing elate of U.S. Provisional Application Ser. No. 62/200,929, entitled "Compound for organic light-emitting diode" filed Aug. 4, 2015 under 35 USC § 119(e)(1).

BACKGROUND OF THE INVENTION

1. Field of the Invention

The present invention relates to a novel compound and an organic electronic device using the same and, more particularly, to a novel compound as hole-blocking type electron-transporters and/or emitters for OLEDs and an organic electronic device using the same.

2. Description of Related Art

It is well known that organic light emitting diode (OLED) was initially invented and proposed fey Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device currently becomes a new generation lighting device or display because of high brightness, fast response speed, light weight, compactness, true color, no difference in viewing angles, without using any LCD backlight plates, and low power consumption.

Recently, some interlayers such as election transport layer and hole transport layer are added between the cathode and the anode for increasing the current efficiency and power efficiency of the OLEDs. For example, an organic light emitting diode (OLED) 1' shown as FIG. 1 is designed to consist of: a cathode 11', an electron injection layer 13', a light emitting layer 14', a hole transport layer 16', and an anode 18'.

In device function concept, the light emitted by the OLED 1' is resulted from excitons produced by the recombination of electrons and holes in the light emitting layer 14'. However, according to theoretical speculation, the ratio of the excitons with singlet excited state and the excitons with triplet excited state is 1:3. So that, when a small molecular fluorescent material is used as the light-emitting layer 14' of the OLED 1', there are about 25% excitons being used in emitting light, and the rest of 75% excitons with triplet excited state are lost through non-luminescence mechanism. For this reason, the general fluorescent material performs a maximum quantum yield of 25% in limit which amounts to an external quantum efficiency of 5% in the device.

Moreover, researches further find that certain hole transport material can simultaneously perform electron confining ability, such as the material represented by following chemical formulas 1' and 2'. The chemical formula 1' represents the chemical structure of Tris(4-carbazoyl-9-ylphenyl) amine, which is called TCTA in abbreviation. The chemical formula 2' represents the chemical structure of N,N'-Di(1-naphthyl)-N,N'-diphenyl-(1,1'-biphenyl)-4,4'-diamine called NPB in abbreviation.

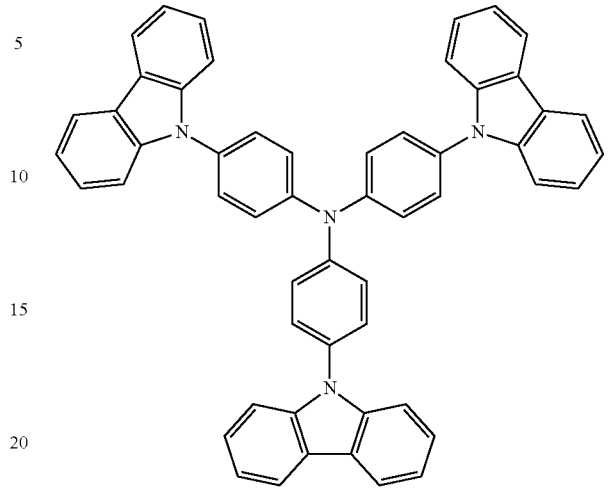

Recently, for effectively increasing the lighting performance of OLEDs, OLED manufactures and researchers have made great efforts to develop electron transport materials with hole blocking functionality, such as TmPyPb, TPBi, 3TPYMB, BmPyPb, and DPyPA represented by following chemical formula 3'-7', respectively. Wherein TmPyPb is the abbreviation of 3,3'-[5'-[3-(3-Pyridinyl)phenyl][1,1':3',1''-terphenyl]-3,3''-diyl]bispyridine, TPBi is the abbreviation of 1,3,5-Tris(1-phenyl-1H-benzimidazol-2-yl)benzene, 3TPYMB is the abbreviation of Tris(2,4,6-triMethyl-3-(pyridin-3-yl)phenyl)borane, BmPyPb is the abbreviation of 1,3-bis(3,5-dipyridin-3-yl-phenyl)benzene, and DPyPA is the abbreviation of 9,10-bis(3-(pyridin-3-yl)phenyl) anthracene.

-continued

[Chemical formula 4']

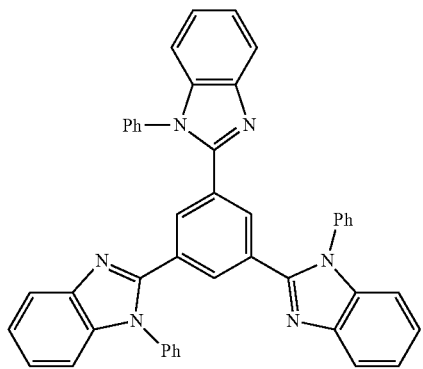

[Chemical formula 5']

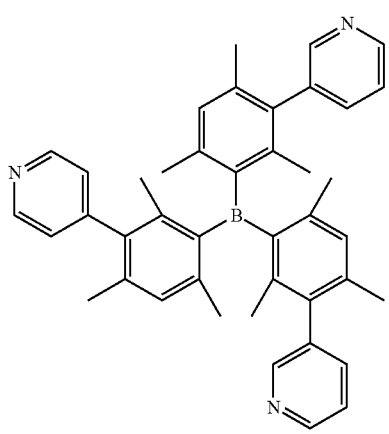

[Chemical formula 6']

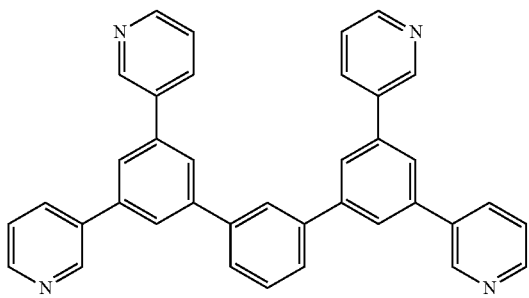

[Chemical formula 7']

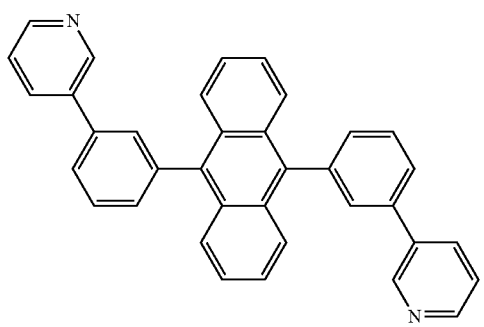

In spite of various electron transport materials with hole blocking functionality have been developed, the phosphorescence OLEDs applied with the said election transport materials still cannot perform outstanding luminous efficiency and device lifetime. Accordingly, in view of the conventional or commercial electron transport materials with hole blocking functionality still including drawbacks, the inventor of the present application has made great efforts to make inventive research thereon and eventually provided novel compounds as hole-blocking type electron-transporters and emitters for OLED.

SUMMARY OF THE INVENTION

The object of the present invention is to provide a novel compound having the function to block holes.

Another object of the present invention is to provide an organic electronic device using the novel compound of the present invention.

To achieve the object, the compound of the present invention comprises a 7-membered ring segment, which is formed by a cis-stilbene segment and a bridge atom with four bonds; and a fluorene segment connecting to the bridge atom with a double bond.

In one aspect of the present invention, the bridge atom is C or Si.

In one preferred aspect of the present invention, the compound is represented by the following formula (I):

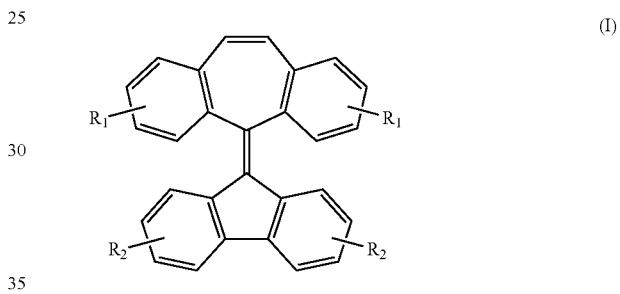

(I)

wherein, each of $R_1$ and $R_2$ independently is H, halogen, aryl heteroaryl or —P(=O)$R_3R_4$, with the proviso that $R_1$ and $R_2$ are not H at the same time; and $R_3$ and $R_4$ are substituents.

Herein, $R_3$ and $R_4$ independently is H, $C_1$-$C_{10}$ alkyl $C_1$-$C_{10}$ alkoxy, $C_3$-$C_{20}$ cycloalkyl, $C_3$-$C_{20}$ heterocycloalkyl, —$NR_aR_b$, aryl or heteroaryl, in which each of $R_a$ and $R_b$ independently is H, $C_1$-$C_{10}$ alkyl, $C_1$-$C_{10}$ alkoxy, $C_3$-$C_{20}$ cycloalkyl $C_3$-$C_{20}$ heterocycloalkyl, aryl, or heteroaryl.

In one aspect of the present invention, $R_1$ is halogen, substituted aryl, or —P(=O)$R_3R_4$; and $R_2$ is H. Preferably, $R_1$ is Br, F,

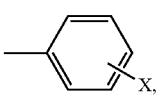

or —P(=O)$R_3R_4$; in which $R_3$ and $R_4$ are phenyl, 4-cyanophenyl or 4-pyridyl, and X is halogen or —CN. More preferably, $R_1$ is F,

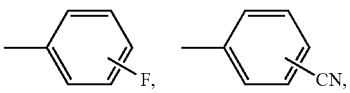

or —P(=O)$R_3R_4$, in which $R_3$ and $R_4$ are phenyl.

In another aspect of the present invention, $R_2$ is halogen, substituted aryl, or —P(=O)$R_3R_4$; and $R_1$ is H. Preferably, $R_2$ is Br, F,

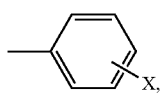

or —P(=O)R$_3$R$_4$; in which R$_3$ and R$_4$ are phenyl 4-cyanophenyl or 4-pyridyl, and X is halogen or —CN. More preferably, R$_2$ is F,

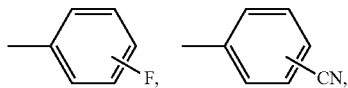

or —P(=O)R$_3$R$_4$, in which R$_3$ and R$_4$ are phenyl.

In one preferred aspect of the present invention, the compound is represented by the following formulas (I-1), (I-2) or (I-3):

(I-1)

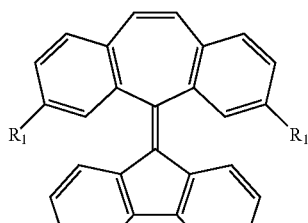

(I-2)

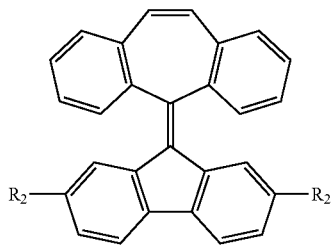

(I-3)

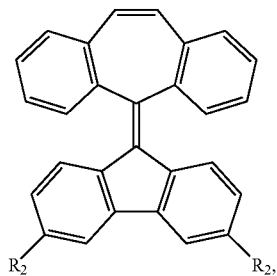

wherein the definitions to R$_1$ and R$_2$ are the same as those illustrated above. Preferably, R$_1$ and R$_2$ are identical. More preferably, R$_1$ and R$_2$ are Br, F,

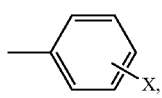

or —P(=O)R$_3$R$_4$; in which X is F or CN, and R$_3$ and R$_4$ are phenyl.

In one preferred aspect of the present invention, the compound is represented by any one of the following formulas (II-1) to (II-3), (III-1) to (III-3) and (IV-1) to (IV-3):

(II-1)

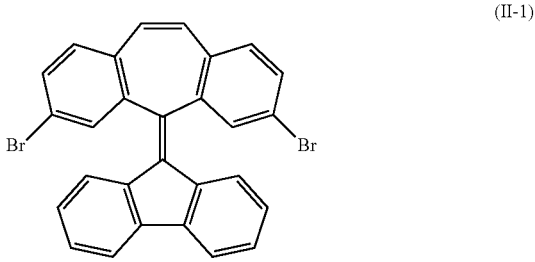

(II-2)

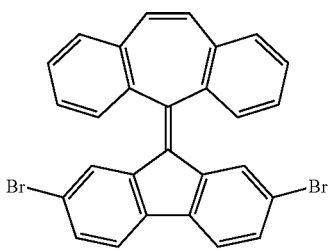

(II-3)

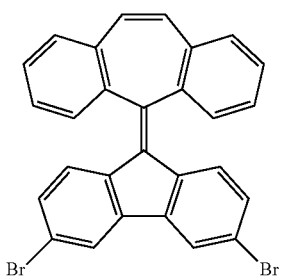

(III-1)

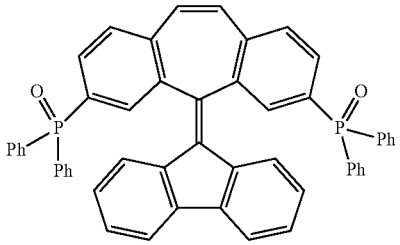

(III-2)

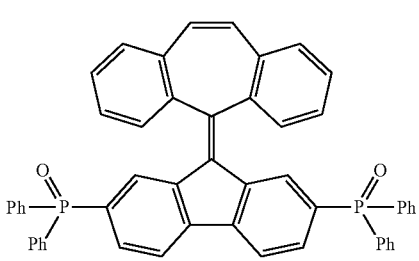

-continued

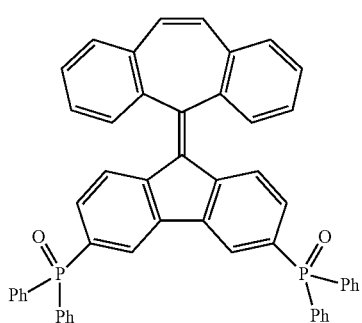
(III-3)

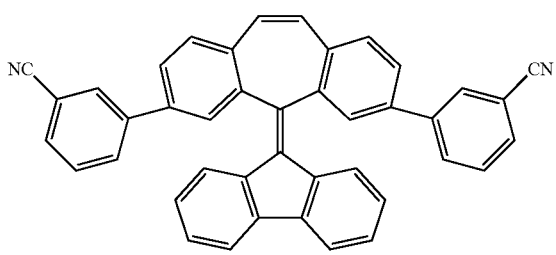
(IV-1)

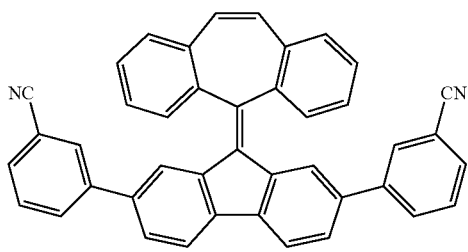
(IV-2)

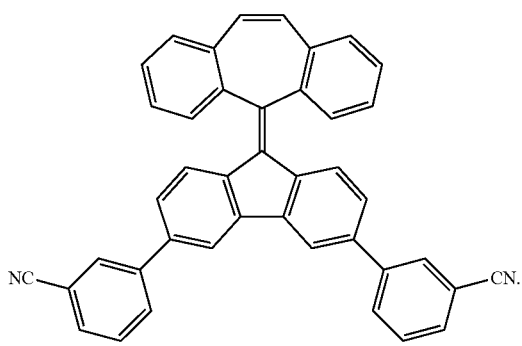
(IV-3)

The present invention provides a novel compound, which is constructed by at least one cis-stilbene based component and at least one fluorene based component that are linked together by a central double bond to form a helicene-configuration. The compound provided by the present invention has good thermal stability, wherein the glass transition temperatures ($T_g$) thereof is ranged from 127° C. to 162° C., and the decomposition temperatures ($T_d$) thereof is ranged from 350° C. to 436° C. In addition, the compound provided by the present invention also has hole blocking property, reversible electron transport property, and balanced charges motilities.

Herein, the compound of the present invention has oxidation potentials ranged from 1.01 V to 1.16 V and reduction potentials ranged from −1.91 V to −2.29 V. Additionally, the compound of the present invention has highest occupied molecular orbital energy levels ($E_{HOMO}$) ranged from 5.95 eV to 6.19 eV and lowest unoccupied molecular orbital energy levels ($E_{LUMO}$) ranged from 2.67 eV to 2.96 eV.

Since the compound provided by the present invention has the aforementioned properties, it can be used in an organic electronic device. Hence, the present invention also provides an organic electronic device, which comprises: a first electrode; a second electrode; and an organic layer disposed between the first electrode and the second electrode, and comprising the compound provided by the present invention.

The application of the organic electronic device of the present invention composes, but is not limited to an organic light emitting device, an organic solar cell device, an organic thin film transistor, an organic photodetector, a flat panel display, a computer monitor, a television, a billboard, a light for interior or exterior illumination, a light for interior or exterior signaling, a heads up display, a fully transparent display, a flexible display, a laser printer, a telephone, a cell phone, a tablet computer; a laptop computer, a digital camera, a camcorder, a viewfinder, a micro-display, a vehicle, a large area wall, a theater or stadium screen, or a sign. Preferably, the organic electronic device of the present invention is applied to an organic light emitting device or as organic solar cell device.

When the organic electronic device of the present invention is used as an organic solar cell device, the organic layer is a carrier transport layer.

When the organic electronic device of the present invention is used as an organic light emitting device, such as an organic light emitting diode (OLED), the compound of the present invention can be used as hole-blocking materials, electron-transporting materials or light-emitting materials light-emitting materials due to the hole blocking property, the reversible electron transport property, and the balanced charges motilities thereof. In this case, the organic layer is an electron transport layer, a hole blocking layer or a light emitting layer; and preferably, the organic layer is the electron transport layer and/or the hole blocking layer.

In the present invention, a variety of experimental data have proved that the compound of the present invention can indeed be used as hole-blocking type electron-transporters and emitting materials for OLEDs; moreover, the experimental data also reveal that the OLEDs using the compound of the present invention can indeed be used as the hole-blocking type electron-transporters and is able to show excellent external quantum efficiency ($\eta_{ext}$), current efficiency ($\eta_c$), power efficiency ($\eta_p$), maximum luminance ($L_{max}$), and device lifetime better than those of phosphorescent OLEDs based on the conventional or commercial electron transport materials.

In the present invention, alkyl, alkoxy, cycloalkyl, heterocycloalkyl, aryl, and heteroaryl present in the compounds include both substituted and unsubstituted moieties, unless specified otherwise. Possible substituents on alkyl, alkoxy, cycloalkyl, heterocycloalkyl, aryl, and heteroaryl include, but are not limited to, alkyl, halogen, alkoxy, heterocyclic group or aryl; but alkyl cannot be substituted with alkyl.

In the present invention, the term "halogen" includes F, Cl, Br and I; and preferably is F or Br. The term "alkyl" refers to linear and branched alkyl; preferably, includes linear or branched $C_{1-10}$ alkyl; and more preferably, includes linear or branched $C_{1-6}$ alkyl. Specific examples of alkyl include, but are not limited to, methyl, ethyl, n-propyl, iso-propyl, n-butyl sec-butyl, iso-butyl, tert-butyl, pentyl, neo-pentyl or hexyl. The term "alkoxy" refers to a moiety that the alkyl defined in the present invention coupled with an oxygen atom; preferably, includes linear or branched $C_{1-10}$ alkoxy; and more preferably, includes linear or branched $C_{1-6}$ alkoxy. Specific examples of alkoxy include, but are not limited to, methoxy, ethoxy, n-propoxy, iso-propoxy, n-butoxy, iso-butoxy, sec-butoxy, tert-butoxy, pentyloxy, neo-pentyloxy or hexyloxy. The term "cycloalkyl" refers to a monovalent saturated hydrocarbon ring system having 3 to 20 carbon atoms; and preferably having 3 to 12 carbon atoms. Specific examples of cycloalkyl include, but are not limited to, cyclopropyl, cyclobutyl, cyclopentyl, cyclohexyl, cycloheptyl, and cyclooctyl. The term "heterocyclic group" refers to a 5-8 membered monocyclic, 8-12 membered bicyclic or 11-14 membered tricyclic heteroaryl or heterocycloalkyl having at least one heteroatom which is selected from the group consisting of O, S and N. Specific examples of heterocyclic group include, but are not limited to, pyridyl, pyrimidinyl, furyl, thiazolyl, imidazolyl or thienyl. The term "aryl" refers to a monovalent 6-carbon monocyclic, 10-carbon bicyclic, or 14-carbon tricyclic aromatic ring system. Specific examples of aryl include, but are not limited to, phenyl, naphthyl, pyrenyl anthracenyl or phenanthryl; and preferably, the aryl is phenyl.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
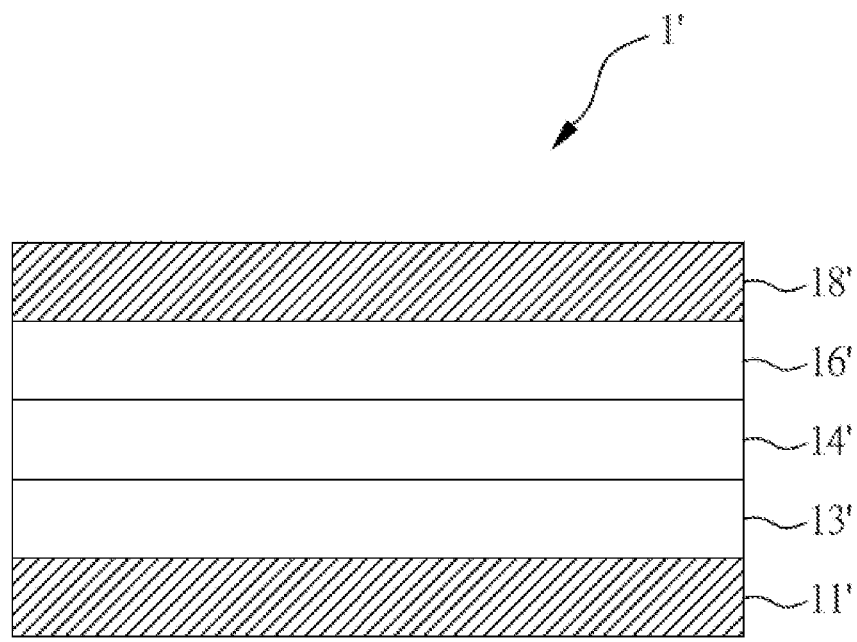
FIG. 1 is a perspective view showing an OLED device of the prior art.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Example 1—Preparation of Compound of Formula (II-1)

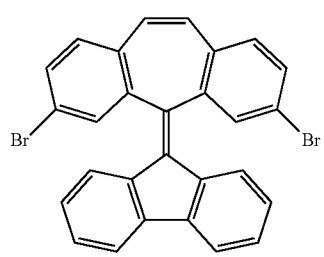

(II-1)

The compound of the formula (II-1) was prepared by using the following steps.

7.0 mmol of fluorene was dissolved in 20 mL of anhydrous tetrahydrofuran (THF), and the obtained solution was stirred in an environment of 0° C. 5.0 mL of H-butyllithium hexanes solution (8 mmol) from a n-butyllithium solution 1.6 M is hexanes was added dropwise info the solution containing fluorene and the obtained solution was stirred for 30 min. Then, 8.4 mmol of neat trimethylsilyl chloride (1 mL) was added thereto, followed by stirring for 3 hours. The reaction mixture was quenched with, saturated aqueous ammonium chloride (15 mL) and the aqueous layer was extracted with $CH_2Cl_2$ (3×20 mL). The organic extracts with sodium sulfate (5 grams) were dried and then concentrated to get the 5-trimethylsilyl-fluorene.

Next, 120 mg of 5-trimethylsilyl-fluorene (0.5 mmol) was dissolved in 7 mL of anhydrous THE, and the reaction flask was cooled to −78° C. 0.3 mL of H-butyllithium in hexanes solution (0.5 mmol) from a n-butyllithium solution 1.5 M in hexanes was then added dropwise into the solution containing 5-trimethylsilyl-fluorene, and the obtained solution was stirred for 30 min. 120 mg of 3,7-dibromo-dibenzosuberenone (0.5 mmol) dissolved in 5 mL of anhydrous THF was dropwise added into the reaction mixture at 0° C. and then the reaction mixture was warmed to ambient temperature and stirred for 24 hours. After 24 hours, 2 mL of water was added into the reaction mixture for executing a quenching reaction, and then THF was removed by rotary evaporation. The product was extracted by using dichloromethane to obtain an extract liquid extract. Then, 1 g magnesium sulfate was added into the extract liquid extract, and the extract liquid extract was sequentially treated with a drying process, a filtering process and a rotary evaporating process to obtain an intermediate product. The intermediate product was then purified by column chromatography ($CH_2Cl_2$/hexanes: 1/5) to obtain clear crystal white solid represented fey the formula (II-1).

Data fertile compound of the formula (II-1): M.W.: 512.23; $^1$H NMR (400 MHz, $CDCl_3$) δ 7.75 (d, J=1.8, 2H), 7.66 (d, J=7.4 Hz, 2H), 7.59 (dd, J=8.1, 2.1 Hz, 2H), 7.39 (t, J=8.2 Hz, 2H), 7.27 (t, J=7.4 Hz, 2H), 7.00 (t, J=7.6 Hz, 2H), 6.97 (s, 2H), 6.51 (d, J=7.9 Hz, 2H); $^{13}$C NMR (100 MHz, $CDCl_3$) δ 140.83, 138.90, 137.28, 137.16, 133.65, 132.58, 130.66, 130.30, 129,98, 128.37, 126.78, 124.93, 122.86, 119.41; TLC $R_f$ 0.42 $CH_2Cl_2$/hexanes, 1/5); HRMS calcd for $C_{28}H_{16}Br_2$: 509.9619, found: 509.9627.

Example 2—Preparation of Compound of Formulas (II-2) and (II-3)

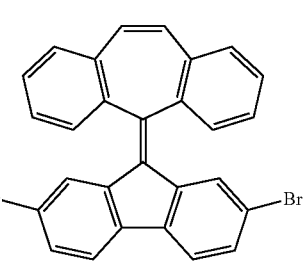

(II-2)

-continued (II-3)
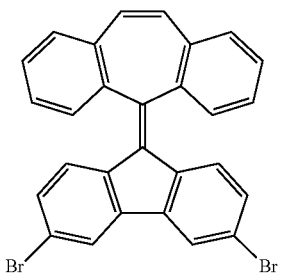

The compounds of the formulas (II-2) and (II-3) were prepared by using the following steps.

5.0 mmol of 2,7- or 3,6-dibromo-9H-fluoren-9-one (1.69 g) was dissolved in 100 mL of anhydrous tetrahydrofuran (THF), and then 2.5 mL of aqueous hydrazine (64% in water) was added thereto. The obtained solution was placed in an environment of 110° C. for refluxing for 8 hours and then concentrated. Next, 96 mmol of oven-dried $MnO_2$ (8.24 g) was added into the reaction solution, and the obtained mixture was stirred for 48 hours at ambient temperature and then concentrated to give a red solid. 4.0 mmol of dibenzosuberen-1-thione (894 mg) was added into the solution with the dissolved red solid in 80 mL of anhydrous toluene to obtain a reaction mixture. After stilling the reaction mixture at 80° C. for 2 hours, the reaction mixture was treated with 5 mmol of triphenylphosphine (1.31 g), followed by refluxing for 1 hour and then cooling to ambient temperature. After filtering off the solid and washing the solid with a solution of hexane/acetone (1/1), an orange solid was obtained which is represented by the formulas (II-2) or (II-3).

Data, for the compound of the formula (II-2): M.W.: 512.23; $^1$H NMR (400 MHz, $CDCl_3$) δ 7.56 (t, J=6.6 Hz, 2H), 7.55 (d, J=6.4 Hz, 2H), 7.51 (dd, J=6.5, 1.0 Hz, 2H), 7.50 (td, J=6.7, 1.8 Hz, 2H), 7.46 (d, J=8.1 Hz, 2H), 7.34 (dd, J=8.1, 1.6 Hz, 2H), 7.05 (s, 2H), 6.51 (s, 2H); $^{13}$C NMR (100 MHz, $CDCl_3$) δ 142.83, 141.12, 137.38, 136.76, 133.37, 131.01, 130.75, 129.88, 128.69, 128.56, 127.73, 126.58, 126.42, 122.59, 122.11; TLC $R_f$ 0.4 (Dichloromethane/hexanes, 1/9); HRMS calcd for $C_{28}H_{16}Br_2$: 509.9619, found: 509.9615.

Data for the compound of the formula (II-3): M.W.: 512.23; $^1$H NMR (400 MHz, $CDCl_3$) δ 7.73 (d, J=1.9 Hz, 2H), 7.53 (dd, J=7.1, 1.4 Hz, 4H), 7.45 (m, 4H), 7.05 (dd, J=8.6, 1.9 Hz, 2H), 7.03 (s, 2H), 6.29 (d, J=8.5 Hz, 2H); $^{13}$C NMR (100 MHz, $CDCl_3$) δ 144.07, 138.36, 138.37, 136.91, 133.32, 130.95, 130.74, 130.70, 128.75, 128.69, 128.42, 127.94, 126.54, 120.65, 120.41; TLC $R_f$ 0.4 (Dichloromethane/hexanes, 1/9); HRMS calcd for $C_{28}H_{16}Br_2$: 509.9619, found: 509.9615.

Example 3—Preparation of Compound of Formulas (III-1) to (III-3)

(III-1)
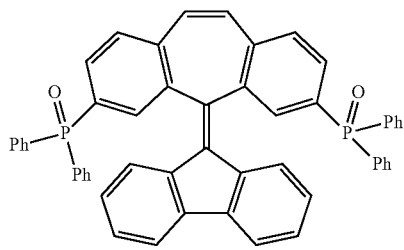

(III-2)

(III-3)
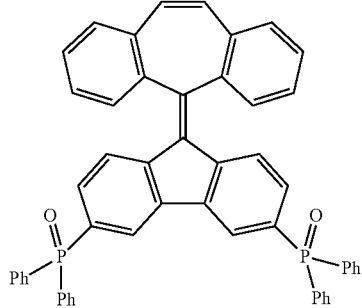

The compounds of the formulas (III-1) to (III-3) were prepared by using the following steps.

The compounds of formulas (II-1) to (II-3) were treated with a lithiation process by using n-butyllithium (1.5 equiv) in anhydrous THF (200 mL) at −78° C. The reaction mixtures were then reacted with chlorodiphenylphosphine (2 equiv) for 2 hours, quenched with water (5 mL), extracted with $CH_2Cl_2$ (3×10 mL), and then concentrated. Next, the reaction mixtures were oxidized with 1 mL of aqueous $H_2O_2$ (35%). After stirring the reaction mixtures for 3 hours, the resulting white solid was rescrystallized from a solution of $CH_2Cl_2$ and ethyl acetate to obtain needle white products having the formulas (III-1) to (III-3).

Data for the compound of the formula (III-1): $T_m$ 271° C. M.W.: 754.79; $^1$H NMR (400 MHz, $CDCl_3$) δ 7.87 (ddd, J=11.5, 8.0, 1.6 Hz, 2H), 7.78 (dd, J=11.8, 1.4 Hz, 2H), 7.66 (m, 10H), 7.56 (d, J=1.6 Hz, 2H), 7.52 (dd, J=7.7, 1.6 Hz, 2H), 7.48 (dd, J=7.6, 1.4 Hz, 2H), 7.40 (m, 8H), 7.19 (td, J=7.4, 0.7 Hz, 2H), 7.14 (s, 2H), 6.70 (td, J=7.4, 1.0 Hz, 2H), 6.22 (d, J=7.8 Hz, 2H); $^{13}$C NMR (100 MHz, $CDCl_3$) δ 140.69, 137.63, 137.52, 137.39, 137.24, 136.76, 134.15, 133.78, 132.76, 132.62, 132.56, 132.00, 131.91, 131.58, 132.52, 131.14, 131.04, 130.95, 128.88, 128.75, 128.57, 128.45, 128.16, 126.40, 124.75, 119.30; $^{31}$P NMR (161.5 MHz, $CDCl_3$) δ 28.95; TLC $R_f$ 0.2 (acetone/hexanes, 1/1); HRMS calcd for $C_{52}H_{36}O_2P_2$: 754.2191, found: 754.2203.

Data for the compound of the formula (III-2): $T_m$ 304° C. M.W.: 754.79; $^1$H NMR (400 MHz, $CDCl_3$) δ 7.87 (m, 4H), 7.58 (m, 6H), 7.51 (m, 6H), 7.40 (m, 8H), 7.33 (dd, J=7.6, 0.8 Hz, 2H), 7.24 (d, J=7.3 Hz, 2H), 7.03 (td, J=7.5, 1.2 Hz, 2H), 6.87 (s, 2H), 6.86 (td, J=7.6, 1.1 Hz, 2H), 6.72 (d, J=12.6 Hz, 2H); $^{13}$C NMR (100 MHz, CDCl$_3$) δ 143.94, 142.51, 138.03, 137.89, 136.70, 133.15, 133.07, 132.93, 132.25, 132.15, 131.97, 131.88, 131.84, 131.63, 130.89, 130.51, 128.60, 128.44, 128.40, 128.31, 128.19, 128.13, 127.53, 125.97, 120.19, 120.06; $^{31}$P NMR (161.5 MHz, CDCl$_3$) δ 29.04; TLC R$_f$ 0.2 (acetone/hexanes, 1/1); HRMS calcd for C$_{52}$H$_{36}$O$_2$P$_2$: 754.2191, found: 754.2197.

Data for the compound of the formula (III-3): T$_m$ 304° C. M.W.; 754.79; $^1$H NMR (400 MHz, CDCl$_3$) δ 7.98 (d, J=11.7 Hz, 2H), 7.62 (m, 8H), 7.53 (m, 8H), 7.44 (m, 12H), 7.20 (ddd, J=12.3, 8.2, 1.4 Hz, 2H), 7.03 (s, 2H), 6.52 (dd, J=8.1, 2.1 Hz, 2H); $^{13}$C NMR (100 MHz, CDCl$_3$) δ 146.21, 141.08, 139.72, 139.59, 137.05, 133.09, 133.07, 132.85, 132.81, 132.31, 132.03, 131.93, 131.82, 131.29, 130.78, 130.64, 128.79, 128.59, 128.54, 128.47, 127.84, 126.29, 124.96, 124.83, 123.18, 123.08; $^{31}$P NMR (161.5 MHz, CDCl$_3$) δ 29.53; TLC R$_f$ 0.4 (acetone/hexanes, 2/1); HRMS calcd for C$_{52}$H$_{36}$O$_2$P$_2$: 754.2191, found: 754.2177.

Example 4—Preparation of Compound of Formulas (IV-1) to (IV-3)

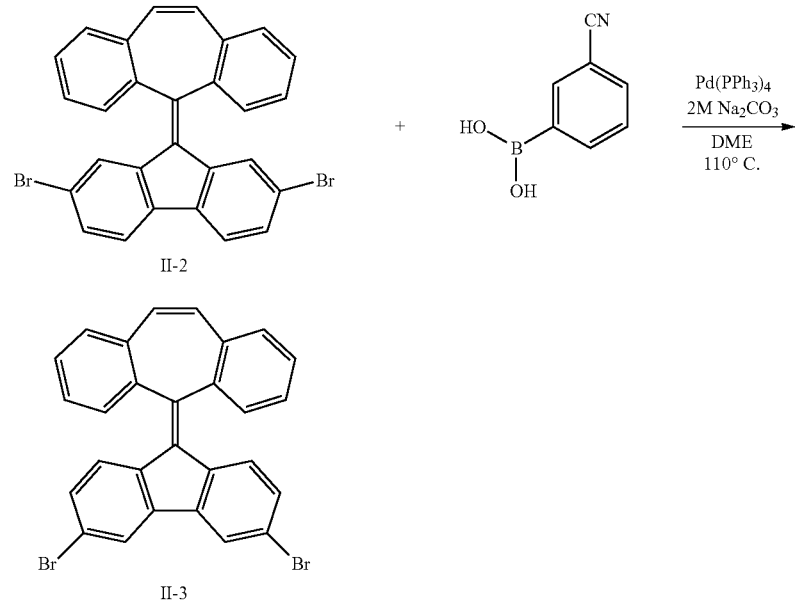

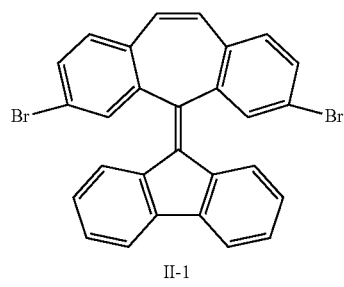

-continued

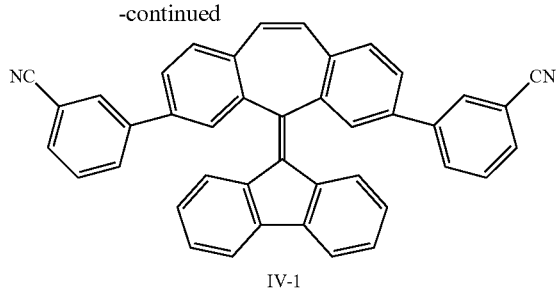

IV-1

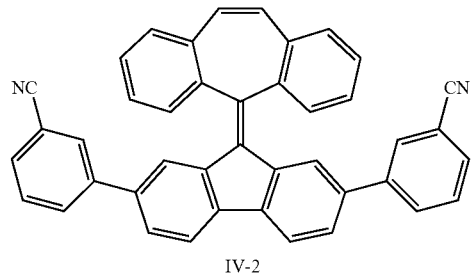

IV-2

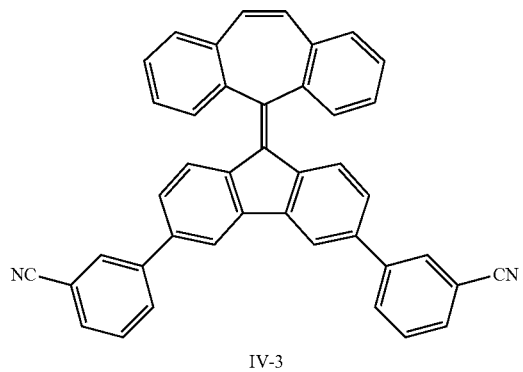

IV-3

A mixture of the compounds from either formula (II-1) to formula (II-3) (1.0 mmol), (3-cyanophenyl)boronic acid (0.323 g, 2.2 mmol), Pd(PPh$_3$)$_4$ (58 mg, 0.05 mmol), and sodium carbonate (1.06 g, 10 mmol) in DME (20 mL) and distilled water (5 mL) was refluxed for 24 h under argon. The mixture was then extracted with CH$_2$Cl$_2$. The combined organic extracts were dried over anhydrous MgSO$_4$ and concentrated by rotary evaporation. The crude product was purified by column chromatography on silica gel using 1:2 CH$_2$Cl$_2$/Hexanes as eluent to afford a white solid. Yields: 72-79%.

Data for the compound of the formula (IV-1): T$_m$ 303° C. M.W.: 556.67; $^1$H NMR (400 MHz, CDCl$_3$) δ 57.88 (s, 2H), 7.82 (dd, J=7.8 Hz, J=0.8 Hz, 2H), 7.70-7.66 (m, 3H), 7.62 (d, J=7.6 Hz, 1H), 7.52 (t, J=7.8 Hz, 1H), 7.27 (t, J=7.4 Hz, 1H), 7.14 (s, 1H), 6.93 (t, J=7.6 Hz, 1H), 6.57 (t, J=8.0 Hz, 1H); $^{13}$C NMR (100 MHz, CDCl$_3$) δ 141.42, 140.81, 139.47, 139.20, 138.24. 137.58, 133.76, 133.49, 131.27, 130.95, 130.85, 130.40, 129.69, 129.54, 128.26, 126.57, 126.16, 125.89, 124.77, 119.49, 118.62, 113.05; TLC R$_f$ 0.10 (CH$_2$Cl$_2$/hexanes, 1/4); HRMS calcd for C$_{42}$H$_{24}$N$_2$: 556.1939, found: 556.1945.

Data for the compound of the formula (IV-2): T$_m$ 297° C. M.W.: 556.67; $^1$H NMR (400 MHz, CDCl$_3$) δ 6.72 (d, J=1.2 Hz, 2H), 7.06 (s, 2H), 7.43-7.51 (m, 4H), 7.55-7.63 (m, 12H), 7.75-7.69 (m, 4H); $^{13}$C NMR (100 MHz, CDCl$_3$) δ 142.93, 142.09, 140.15, 139.35, 137.52, 136.73, 133.97, 132.08, 131.07, 130.88, 130.52, 130.48, 129.64, 129.23, 128.89, 128.06, 127.16, 126.45, 124.15, 120.34, 118.97, 113.04; TLC R$_f$ 0.40 (CH2Cl2/hexanes, 1/2): HRMS calcd for C$_{42}$H$_{24}$N$_2$: 556.1939, found: 556.1938.

Data for the compound of the formula (IV-3): T$_m$ 302° C. M.W.: 556.67; $^1$H NMR (400 MHz, CDCl$_3$) δ 6.58 (d, J=8.4 Hz, 2H), 7.08 (s, 2H), 7.17 (dd, J=8.4 Hz, 1.6 Hz, 2H), 7.46-7.64 (m, 12H), 7.51 (dd, J=7.6 Hz, 1.2 Hz, 2H), 7.91 (dd, J=4.8 Hz, 1.2 Hz, 4H). $^{13}$C NMR (100 MHz, CDCl$_3$) δ 143.24, 142.29, 141.10, 138.54, 137.80, 133.70, 131.78, 131.49, 131.00, 130.77, 129.82, 128.91, 128.79, 127.92, 127.03, 125.97, 125.92, 118.99, 117.93, 113.20: TLC R$_f$ 0.38 (CH$_2$Cl$_2$/hexanes, 1/2); HRMS calcd for C$_{42}$H$_{24}$N$_2$: 556.1939, found: 556.1943.

Steady-State Photophysical Measurements

Absorption spectra were measured on a SP-8001 Diode Array spectrometer by using spectrophotometric grade CH$_2$Cl$_2$ (10 mM in CH$_2$Cl$_2$). Emission spectra (in 10 mM) were measured on a FP-6500 luminescence spectrometer upon excitation at the absorption maxima, of the longest absorption band in the same solvent. The emission spectra measured in CH$_2$Cl$_2$ (10 mM) were normalized by their emission maxima to the same intensity (maximum intensity 1). Fluorescence quantum yield ($\Phi_f$, %) calculation were integrated emission area of the fluorescent spectra and compared the value to the same area measured for Coumarin 1[2c] ($\Phi_f$=0.90, $CH_2Cl_2$) or Coumarin 6 ($\Phi_f$=0.78, EtOH) in $CH_2Cl_2$ (in 10 mM). The quantum yields are calculated by using the following equation 1. Where A stands for area of fluorescent emission for sample (i.e. the compounds of formulas (III-1) to (III-3)) and Coumarin 1 or Coumarin 6; a is absorbance for sample and Coumarin 1 or Coumarin 6; and n is the refractive indices of solvent for sample and Coumarin 1 or Coumarin 6 (the refractive index (n) for $CH_2Cl_2$=1.42; for EtOH=1.36).

$$\Phi^{sample}_f = (A_{sample}/A_{standard}) \times (a_{standard}/a_{sample}) \times (n_{sample}/n_{sample}) \times (n_{sample}/n_{standard})^2 \times \Phi^{standard}_f \quad \text{[Equation 1]}$$

Cyclic Voltammetry (CV) Measurements

CV experiments were carried out with 1.0 mM of one substrate in a given anhydrous, degassed solvent containing 0.1 M tetrabutylammonium perchlorate or phosphate (n-$Bu_4NClO_4$ or n-$Bu_4NPF_6$) as a supporting electrolyte on a Chinstruments CH1604A potentiostat. A platinum wire electrode was used as a counter electrode, and a glassy carbon electrode was used as a working electrode. Ag/AgCl was used as a reference electrode.

Differential Scanning Calorimetry (DSC) Analyses

DSC measurements were performed on a SEIKO SSC 5200 DSC Computer/Thermal Analyzer. The samples were first heated (20° C./min) to melt and then quenched with liquid nitrogen. Glass transition temperatures ($T_g$) were recorded by heating (10° C./min) the cooled samples.

Thermogravimetric Analyses (TGA)

TGA measurements were performed on a SEIKO TG/DTA200 instrument by the Northern Instrument Center of Taiwan. Melting points were measured on a Hargo MP-2D instrument.

Property Evaluations of Compounds of Formulas (III-1) to (III-3) and (IV-1) to (IV-3)

The data of glass transition temperature ($T_g$), decomposition temperature ($T_d$), the longest peak wavelength value of absorption spectrum ($\lambda_{max}$), and the longest peak wavelength value of photoluminescence spectrum (PL $\lambda_{max}$) of the compounds of formulas (III-1) to (III-3) and (IV-1) to (IV-3) are measured and recorded in the following Table 1. From the Table (1), it is able to know that these compounds provided by the present invention have glass transition temperatures ($T_g$) ranged from 127° C. to 162° C. and decomposition temperatures ($T_d$) ranged from 350° C. to 436° C. That means the compounds of provided by the present invention possess excellent thermal stability, and are not easy to decompose under high voltage and high current density operation conditions.

TABLE 1

| Compound | $T_g$ (° C.) | $T_d$ (° C.) | $\lambda_{max}$ (nm) | PL$\lambda_{max}$ (nm) |
|---|---|---|---|---|
| Formula (III-1) | 140 | 350 | 308 | 491 |
| Formula (III-2) | 143 | 375 | 303 | 459 |
| Formula (III-3) | 162 | 357 | 329 | 473 |
| Formula (IV-1) | 143 | 436 | 320 | 469, 503 |
| Formula (IV-2) | 127 | 363 | 334 | 468, 496 |
| Formula (IV-3) | 161 | 346 | 338 | 464, 497 |

Moreover, the oxidation potential and the reduction potential of the compounds provided by the present invention can be measured by way of cyclic voltammetry (CV); therefore, the highest occupied molecular orbital energy level ($E_{HOMO}$) and lowest unoccupied molecular orbital energy level ($E_{LUMO}$) of the compounds provided by the present invention can also be calculated based on the measured oxidation potential ($E_{1/2}^{ox}$) and the reduction potential ($E_{1/2}^{red}$). With reference to following Table 2, $E_{1/2}^{ox}$, $E_{1/2}^{red}$, $E_{HOMO}$, and $E_{LUMO}$ of the compounds of the present invention are recorded. From the Table 2, the persons skilled in OLED material art are able to know that the compounds provided by the present invention have the $E_{HOMO}$ ranged from 5.95 eV to 6.19 eV and the $E_{LUMO}$ ranged from 2.67 eV to 2.96 eV. Moreover, the compounds provided by the present invention also have the oxidation potentials ranged from 1.01 V to 1.16 V and the reduction potentials ranged from −1.91 V to −2.29 V.

TABLE 2

| Compound | $E_{1/2}^{ox}$ (V) | $E_{1/2}^{red}$ (V) | $E_g$ (eV) | $E_{HOMO}$ (eV) | $E_{LUMO}$ (eV) |
|---|---|---|---|---|---|
| Formula (III-1) | 1.09 | −2.29 | 3.40 | 6.19 | 2.79 |
| Formula (III-2) | 1.05 | −2.02 | 3.28 | 6.15 | 2.87 |
| Formula (III-3) | 1.16 | −1.91 | 3.20 | 6.16 | 2.96 |
| Formula (IV-1) | 1.04 | −2.17 | 3.35 | 6.14 | 275 |
| Formula (IV-2) | 1.01 | −2.18 | 3.37 | 5.98 | 2.67 |
| Formula (IV-3) | 1.07 | −2.12 | 3.25 | 5.95 | 2.82 |

Furthermore, on order to prove that the compounds of the present invention can indeed be applied in OLEDs for being as a hole-blocking type electron transport layer, a plurality of OLED devices for control groups and experiment groups have been designed and manufactured.

All the materials were either commercially available or synthesized as described in this experiment and were subjected to gradient sublimation under high vacuum prior to use. The substrate was an indium tin oxide (ITO) coated glass sheet with a sheet resistance of ~30 W/▫. Pre-patterned ITO substrates were cleaned sequentially by sonication in a detergent solution, doubly distilled water, and EtOH for 5 min in turn before being blown dry with a stream of nitrogen. The ITO substrate was then treated with oxygen plasma for 5 min before being loaded into the vacuum chamber. The organic layers were deposited thermally at a rate of 0.1-0.3 nm/s in a chamber (ULVAC, TU-12RE) under a pressure of 5×10$^{-6}$ Torr. Device were constructed with 40 nm of the hole transporting layer (HTL), 40 nm of the light-emitting layer (LEL), 10 nm of the hole-blocking layer (HBL), 40 nm of the electron-transporting layer (ETL), 1 nm of LiF as the electron-injecting layer (EIL), and 150 nm of Al as the cathode, respectively. In addition, 1,4,5,8,9,11-Hexaazatriphenylene-hexacarbonitrile (HATCN) is used as the HIL; 4,4-Cyclohexylidenebis [N,N-bis(4-methylphenyl) benzenamine] (TAPC) is used as the HT01. Herein, the material used in each layer is summarized in the following Table 3.

TABLE 3

| | Cathode | EIL | ETL | HBL | LEL | HTL | Anode |
|---|---|---|---|---|---|---|---|
| Embodiment 1 | Al | LiF | Formula (III-1) | Formula (III-1) | Green phosphorescent | TAPC | HIL/ITO |

TABLE 3-continued

| | Cathode | EIL | ETL | HBL | LEL | HTL | Anode |
|---|---|---|---|---|---|---|---|
| Embodiment 2 | Al | LiF | Formula (III-2) | Formula (III-2) | Green phosphorescent | TAPC | HIL/ITO |
| Embodiment 3 | Al | LiF | Formula (III-3) | Formula (III-3) | Green phosphorescent | TAPC | HIL/ITO |
| Embodiment 4 | Al | LiF | Formula (IV-1) | Formula (IV-1) | Green phosphorescent | TAPC | HIL/ITO |
| Embodiment 5 | Al | LiF | Formula (IV-2) | Formula (IV-2) | Green phosphorescent | TAPC | HIL/ITO |
| Embodiment 6 | Al | LiF | Formula (IV-3) | Formula (IV-3) | Green phosphorescent | TAPC | HIL/ITO |
| Comparative embodiment 1A | Al | LiF | BmPyPb | BmPyPb | Green phosphorescent | TAPC | HIL/ITO |
| Comparative embodiment 1B | Al | LiF | DPyPA | DPyPA | Green phosphorescent | TAPC | HIL/ITO |
| Comparative embodiment 1C | Al | LiF | TPBi | TPBi | Green phosphorescent | TAPC | HIL/ITO |
| Comparative embodiment 1D | Al | LiF | ET01 | ET01 | Green phosphorescent | TAPC | HIL/ITO |
| Embodiment 7 | Al | LiF | Formula (III-3) | Formula (III-3) | Green phosphorescent | NPB/HT01 | HIL/ITO |
| Embodiment 8 | Al | LiF | Formula (IV-3) | Formula (IV-3) | Green phosphorescent | NPB/HT01 | HIL/ITO |
| Comparative embodiment 2 | Al | LiF | BmPyPb | BmPyPp | Green phosphorescent | NPB/HT01 | HIL/ITO |
| Comparative embodiment 3 | Al | LiF | ET01 | ET01 | Green phosphorescent | NPB/HT01 | HIL/ITO |

In the Table 3, BmPyPb is the abbreviation of 1,3-bis(3,5-dipyrid-3-yl-phenyl)benzene, DPyPA is the abbreviation of 9,10-bis(3-(pyridin-3-yl)phenyl)anthracene, mid TPBi is the abbreviation of 1,3,5-Tris(1-phenyl-1H-benzimidazol-2-yl)benzene. In addition, ET01 is represented by the following formula (TV) and the green phosphorescent dopant is Ir(ppy)$_3$ along with 11-(4,6-diphenyl-1,3,5-triazin-2-yl)-12-phenyl-11,12-dihydroindolo[2,3-a]carbazole as the host which is represented by the following formula (V).

(IV)

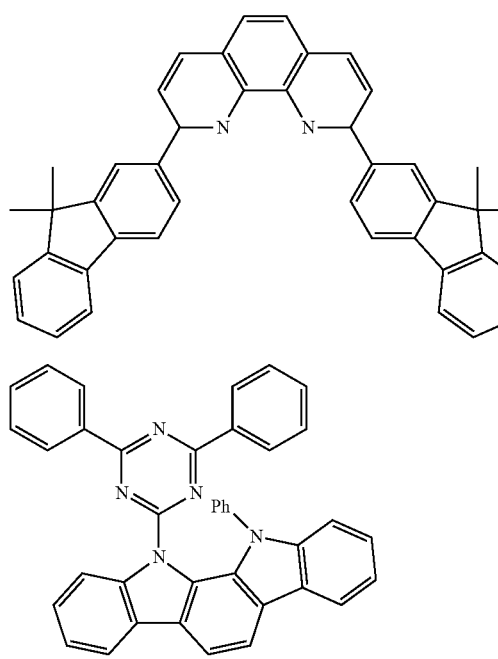

(V)

Furthermore, it is able to know that the materials of TPBi, DPyPA, BmPyPb, and ET01 recorded in the Table 3 are also used as OLED device's electron transport layers. However, the present invention is not limited thereto.

Figure 2:
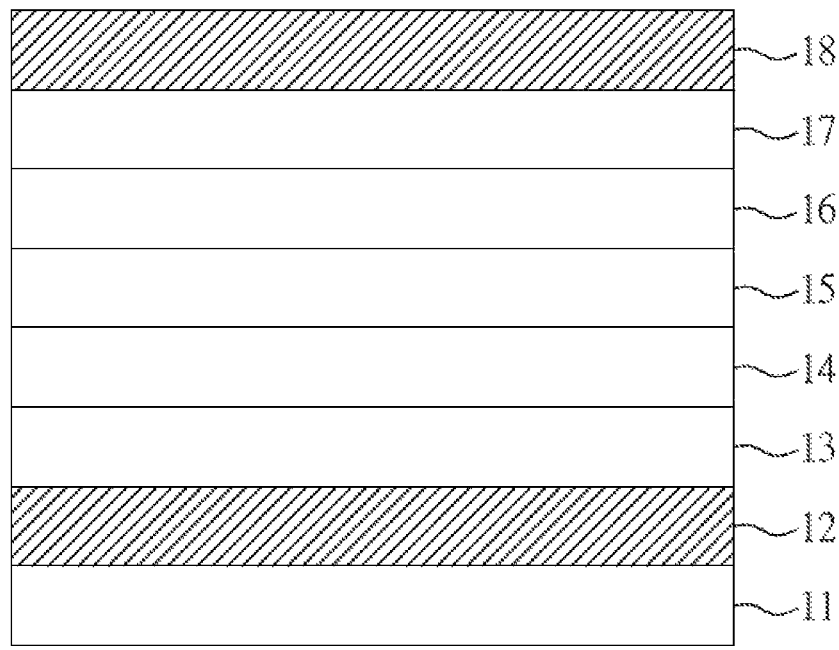
FIG. 2 is a perspective view showing an OLED device of the present invention.

FIG. 2 is a perspective view showing the OLED devices provided above. The OLED device of the present invention comprises: a first electrode 12; a second electrode 18; and an organic layer disposed between the first electrode 12 and the second electrode 18. Herein, the first electrode 12 is a cathode, and a substrate 11 is disposed therebelow. The second electrode 18 is an anode. The organic layer comprises: an election-injection layer 13, an electrode-transporting layer 14, a hole-blocking layer 15, a light-emitting layer 16, and a hole transporting layer 17, sequentially laminated on the first electrode 12.

Herein, Current-voltage-light intensity (I-V-L) characteristics and EL spectra were measured and recorded by PRECISE GAUGE, EL-1003; and the turn-on voltage ($V_{on}$), the external quantum efficiency ($\eta_{ext}$), the current efficiency ($\eta_c$), the power efficiency ($\eta_p$), and the maximum luminance ($L_{max}$) of the OLED devices are listed in the following Table 4.

TABLE 4

| | $\lambda_{max}$ (nm) | Von (V) | $\eta_{ext}$ (%) | $\eta_p/\eta_c$ (%) | $L_{max}$ (cd/m$_2$) |
|---|---|---|---|---|---|
| Embodiment 1 | 516 | 2.1 | 10.8 | 38.8/20.9 | 109,500 |
| Embodiment 2 | 512 | 2.2 | 13.3 | 46.7/20.7 | 123,800 LT$_{50}$, 2,700 h |
| Embodiment 3 | 516 | 2.2 | 13.2 | 46.9/18.0 | 62,840 |
| Embodiment 4 | 512 | 2.1 | 10.5 | 50.6/37.2 | 127,610 LT$_{50}$, 14,700 h |
| Embodiment 5 | 512 | 2.2 | 11.8 | 49.4/36.7 | 126,353 |
| Embodiment 6 | 512 | 2.4 | 10.9 | 48.9/36.1 | 125,789 |
| Comparative embodiment 1A | 516 | 2.5 | 6.3 | 22.8/18.0 | 142,100 LT$_{50}$, 1,000 h |
| Comparative embodiment 1B | 516 | 3.0 | 10.2 | 37.8/24.0 | 40,700 |
| Comparative embodiment 1C | 516 | 3.0 | 6.9 | 24.7/22.0 | 37,640 |

TABLE 4-continued

| | $\lambda_{max}$ (nm) | Von (V) | $\eta_{ext}$ (%) | $\eta_p/\eta_c$ (%) | $L_{max}$ (cd/m$_2$) |
|---|---|---|---|---|---|
| Comparative embodiment 1D | 512 | 2.0 | 14.5 | 51.1/31.2 | 124,200 LT$_{50}$, 13,500 h |
| Embodiment 7 | 516 | 5.0 | 11.9 | 40.7/25.6 | 41,000 LT$_{50}$, 3,022 h |
| Embodiment 8 | 516 | 5.0 | 12.5 | 43.5/28.6 | 52,700 LT$_{50}$, 6,040 h |
| Comparative embodiment 2 | 516 | 4.5 | 10.8 | 36.8/25.7 | 42,150 |
| Comparative embodiment 3 | 516 | 5.5 | 7.04 | 26.2/14.9 | 26,000 LT$_{50}$, 600 h |

With reference to the measured data of the green phosphorescent OLED devices in the Table 4, one can find that the OLED devices using single hole transport layer of Embodiments 1-3 and Embodiments 4-6 show excellent $\eta_{ext}$, $\eta_c$, $\eta_p$, and $L_{max}$ and are much superior to the OLED devices using single hole transport layer of Comparative embodiment 1A, Comparative embodiment 1B, and Comparative embodiment 1C. Among them, Embodiment 2 (Compound of formula (III-2)) and Embodiment 5 (Compound of formula (IV-2)) show the best and comparable results with that for Comparative embodiment 1D. For the OLED device of Embodiment 2, the $\eta_{ext}$ is 13.3%, $\eta_0$ is 46.7 cd/A, $\eta_c$ is 20.7 lm/w, and $L_{max}$ is 123,800 cd/m$^2$. For the OLED device of Embodiment 4, the $\eta_{ext}$ is 10.5%, $\eta_p$ is 50.6 cd/A, $\eta_c$ is 37.2 lm/w, and $L_{max}$ is 127,600 cd/m$^2$.

In addition, the data shown in Table 1 also reveal that the OLED devices using single hole transport layer of Embodiments 7 and 8 show excellent $\eta_{ext}$, $\eta_c$, $\eta_p$, and $L_{max}$ and are superior to the OLED devices using complex (i.e., double) hole transport layer of Comparative embodiment 2 and Comparative embodiment 3. Moreover, the OLED device using complex (double) hole transport layer of Embodiment 7 (Compound of formula (III-3)) and Embodiment 8 (Compound of formula (IV-3)) also shows excellent $\eta_{ext}$, $\eta_c$, $\eta_p$, and $L_{max}$, which is superior to the OLED devices using complex (i.e., double) hole transport layer of Comparative embodiment 2 and Comparative embodiment 3.

Furthermore, device life time evaluation test for the green phosphorescent OLEDs have also been completed based on a starting luminance of 10,000 cd/cm$^2$. Life time evaluation test results reveal that the decay half lifetimes (LT$_{50}$) of the green phosphorescent OLED for Embodiment 4, Embodiment 7 and Embodiment 8 are 14,700 hours, 3,022 hours and 6,040 hours, respectively. In addition, the decay half lifetime (LT$_{50}$) for the green phosphorescent OLEDs of Comparative embodiment 1A, Comparative embodiment 1D, and Comparative embodiment 3 are respectively measured as 1,000, 13,500, and 600 hours.

In conclusion, the compounds of the present invention have glass transition temperatures ranged from 127° C. to 162° C., decomposition temperatures ranged from 350° C. to 436° C., reversible electron transport, property, and balanced charges motilities.

Moreover, a variety of experimental data have proved that the compounds of the present invention can indeed be used as a hole-blocking type electron-transporter for OLEDs; moreover, the experimental data also reveal that the OLEDs using the compounds of the present invention can show excellent external quantum efficiency ($\eta_{ext}$), current efficiency ($\eta_c$), power efficiency ($\eta_p$), maximum luminance ($L_{max}$), and device lifetime performances better than the conventional or commercial OLEDs.

Figure 3:
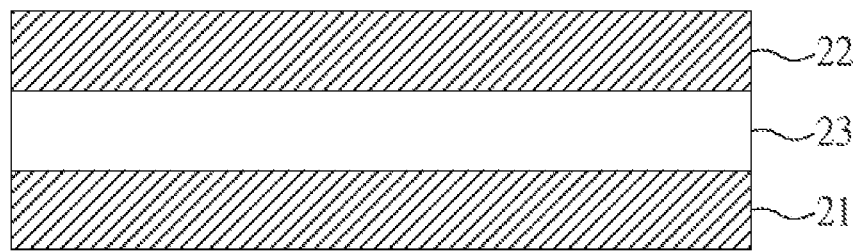
FIG. 3 is a perspective view showing an organic solar cell device of the present invention.

Except for the aforementioned OLED devices, the present invention also provides an organic solar cell, which is shown in FIG. 3. The organic solar cell of one embodiment of the present invention comprises: a first electrode 21; a second electrode 22; and an organic layer 23 disposed between the first electrode 21 and the second electrode 22 and comprising any one of the compounds of the formulas (III-1) to (III-3) or the formulas (IV-1) to (IV-3). In the organic solar cell of the present invention, the organic layer 23 is served as a carrier transport layer.

Except for the aforementioned OLED device and organic solar cell device, the compounds provided by the present invention can be applied to various organic electronic devices, such as an organic thin film transistor, an organic photodetector, a flat panel display a computer monitor, a television, a billboard, a light for inferior or exterior illumination, a light for interior or exterior signaling, a heads up display a fully transparent display, a flexible display, a laser printer, a telephone, a cell phone, a tablet computer, a laptop computer, a digital camera, a camcorder, a viewfinder, a micro-display a vehicle, a large area wall, a theater or stadium screen, or a sign. However, the present invention is not limited thereto.

Although the present invention has been explained in relation to its preferred embodiment, it is to be understood that many other possible modifications and variations can be made without departing from the spirit and scope of the invention as hereinafter claimed.

What is claimed is:

1. A compound represented by the following formula (I-1) or (I-3):

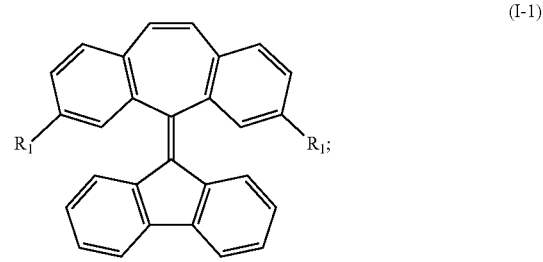 [SMILES: Brc1ccc2c(c1)C(=C1c3ccccc3-c3ccccc31)c1cc(Br)ccc1C=C2]

(I-1)

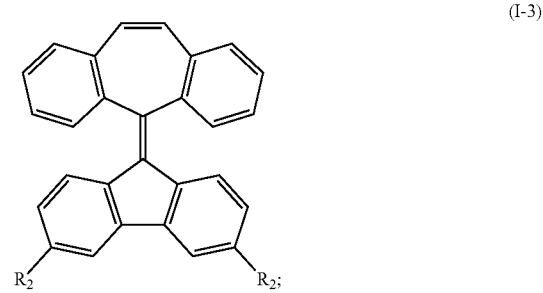

(I-3)

wherein R$_1$ is aryl, heteroaryl, or —P(=O)R$_3$R$_4$;
wherein R$_2$ is halogen, aryl, heteroaryl, or —P(=O)R$_3$R$_4$;
wherein each of R$_3$ and R$_4$ independently is H, C$_1$-C$_{10}$ alkyl, C$_1$-C$_{10}$ alkoxy, C$_3$-C$_{20}$ cycloalkyl, C$_3$-C$_{20}$ heterocycloalkyl, —NR$_a$R$_b$, aryl, or heteroaryl, in which each of R$_a$ and R$_b$ independently is H, C$_1$-C$_{10}$ alkyl, C$_1$-C$_{10}$ alkoxy, C$_3$-C$_{20}$ cycloalkyl, C$_3$-C$_{20}$ heterocycloalkyl, aryl, or heteroaryl.

2. The compound of claim 1, wherein R$_1$ is substituted aryl, substituted heteroaryl, or —P(=O)R$_3$R$_4$.

3. The compound of claim 2, wherein $R_1$ is

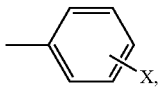

substituted heteroaryl, or —P(=O)$R_3R_4$; in which $R_3$ and $R_4$ are phenyl, 4-cyanophenyl or 4-pyridyl, and X is halogen or —CN.

4. The compound of claim 3, wherein $R_1$ is

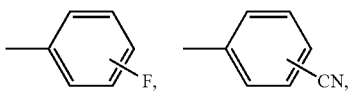

or —P(=O)$R_3R_4$, in which $R_3$ and $R_4$ are phenyl.

5. The compound of claim 1, wherein $R_2$ is Br, F,

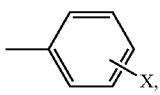

or —P(=O)$R_3R_4$; in which $R_3$ and $R_4$ are phenyl, 4-cyanophenyl or 4-pyridyl, and X is halogen or —CN.

6. The compound of claim 5, wherein $R_2$ is F,

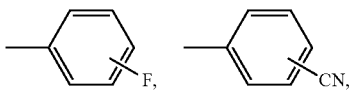

or —P(=O)$R_3R_4$, in which $R_3$ and $R_4$ are phenyl.

7. The compound of claim 1, which has glass transition temperatures ($T_g$) ranging from 127° C. to 162° C., decomposition temperatures ($T_d$) ranging from 350° C. to 436° C., oxidation potentials ranging from 1.01 V to 1.16 V, reduction potentials ranging from −1.91 V to −2.29 V, highest occupied molecular orbital energy levels ($E_{HOMO}$) ranging from 5.95 eV to 6.19 eV and/or lowest unoccupied molecular orbital energy levels ($E_{LUMO}$) ranging from 2.67 eV to 2.96 eV.

8. The compound of claim 1, which is represented by any one of the following formulas (III-1), (III-3), (IV-1), and (IV-3):

(III-1)

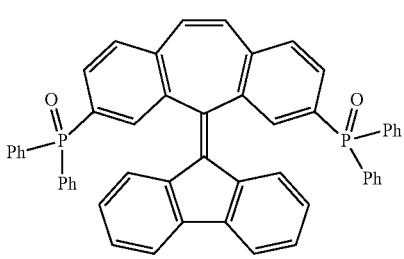

(III-3)

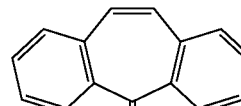

(IV-1)

(IV-3)

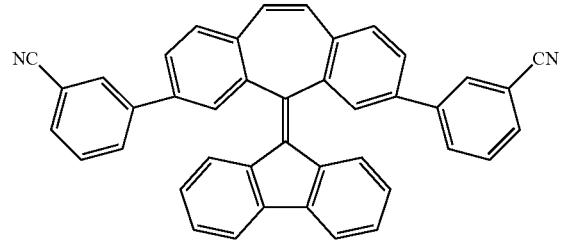

9. The compound of claim 1, which is applied in an organic light emitting diode (OLED) as hole-blocking materials, electron-transporting materials or light-emitting materials.

10. An organic electronic device, comprising:
a first electrode;
a second electrode; and
an organic layer disposed between the first electrode and the second electrode, and comprising a compound represented by following formula (I-1) or (I-3):

(I-1)

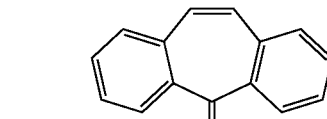

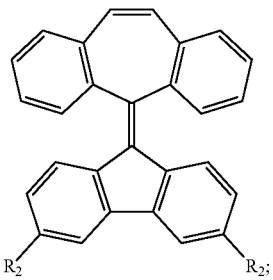

(I-3)

wherein $R_1$ is aryl, heteroaryl, or —P(=O)$R_3R_4$;
wherein $R_{2'}$ is halogen, aryl, heteroaryl, or —P(=O)$R_3R_4$;
wherein each of $R_3$ and $R_4$ independently is H, $C_1$-$C_{10}$ alkyl, $C_1$-$C_{10}$ alkoxy, $C_3$-$C_{20}$ cycloalkyl, $C_3$-$C_{20}$ heterocycloalkyl, —$NR_aR_b$, aryl, or heteroaryl, in which each of $R_a$ and $R_b$ independently is H, $C_1$-$C_{10}$ alkyl, $C_1$-$C_{10}$ alkoxy, $C_3$-$C_{20}$ cycloalkyl, $C_3$-$C_{20}$ heterocycloalkyl, aryl, or heteroaryl.

11. The organic electronic device of claim 10, wherein the organic electronic device is an organic light emitting device, and the organic layer is an electron transport layer or a hole blocking layer.

12. The organic electronic device of claim 10, wherein the organic electronic device is an organic solar cell device, and the organic layer is a carrier transport layer.

* * * * *